United States Patent [19]

Commandeur et al.

[11] Patent Number: 4,956,120
[45] Date of Patent: Sep. 11, 1990

[54] POLYARYLALKANE OLIGOMER COMPOSITIONS AND PROCESS FOR THEIR MANUFACTURE

[75] Inventors: Raymond Commandeur, Vizile; Bernard Gurtner, Grenoble, both of France

[73] Assignee: Atochem, France

[21] Appl. No.: 214,304

[22] Filed: Jul. 1, 1988

[30] Foreign Application Priority Data

Jul. 16, 1987 [FR] France ................................ 87 10067
Oct. 8, 1987 [FR] France ................................ 87 13912

[51] Int. Cl.$^5$ ................................................ B01F 1/00
[52] U.S. Cl. ................................ 252/364; 428/402.2; 503/213; 585/11; 585/19; 585/25; 585/320
[58] Field of Search .................... 252/364; 503/213; 585/11, 19, 25, 320

[56] References Cited

U.S. PATENT DOCUMENTS

| | | | |
|---|---|---|---|
| 3,846,331 | 11/1974 | Konishi et al. | 252/364 |
| 4,251,675 | 2/1981 | Engel | 585/469 X |
| 4,523,044 | 6/1985 | Commandeur et al. | 585/11 |
| 4,737,189 | 4/1988 | Nakamura et al. | 503/213 X |

*Primary Examiner*—Richard D. Lovering
*Attorney, Agent, or Firm*—Sigalos, Levine & Montgomery

[57] ABSTRACT

Polyarylalkane oligomer compositions containing essentially of a mixture of isomers of benzylcumene and its higher homologues and a mixture of isomers of bis-(isopropylphenyl)phenylmethane; the method of making such compositions by first reacting chlorine with toluene, xylene, or a mixture of toluene and xylene in the presence of a radical generator, removing the unreacted toluene and/or xylene, and then subjecting the reaction product to the action of an inorganic halide or of an inorganic acid in the presence of a benzene-related compound; and microcapsules containing color-forming material wherein the compositions are used as solvents for the color-forming material.

11 Claims, No Drawings

POLYARYLALKANE OLIGOMER COMPOSITIONS AND PROCESS FOR THEIR MANUFACTURE

BACKGROUND OF THE INVENTION

The present invention relates to new polyarylalkane oligomer compositions, a process for their manufacture, and products utilizing such compositions.

These products can be used as a microencapsulation solvent for rupturable microcapsules used to make carbonless transfer paper and for other products for which microcapsules can be used.

In Patent EP No. 136,230, the person skilled in the art has already proposed mixtures of oligomers based on benzyltoluene, dibenzyltoluene and ditolylphenylmethane, which exhibit the advantage, when compared with these same oligomers taken separately, of crystallizing at very low temperature and of having a viscosity which is always compatible with their application as a dielectric for capacitors. These characteristics make them most particularly suitable for use as a microencapsulation solvent for microcapsules for such uses as in making carbonless transfer paper. However, they have a characteristic which disqualifies them for such use; namely, a highly unpleasant odor which is disclosed just like the color when the microcapsules are ruptured, at the time of hitting the keys of a typewriter, for example. The compositions according to the invention not only have a viscosity which is compatible with the application, but are also characterized by an "absence of odor" which is absolutely essential in the intended application as a microencapsulation solvent for forming microcapsules.

Patent GB No. 1,346,364 summarizes the properties which must be reconciled in microencapsulation solvents:

(i) dissolving the dye, (ii) not evaporating when the microcapsules are processed, (iii) being inert towards the encapsulation material, (iv) not reacting with the solvent developer, (v) having a viscosity which is low and relatively insensitive to temperature, and (vi) not having an unpleasant odor.

Since the disadvantages of mono- and dibenzylalkylbenzenes have also long been known, many substitute mixtures have been proposed, starting with polyarylalkane oligomers. However, it is always difficult to reconcile the quality of the properties of the products obtained with the economic aspect of the means for producing this substitute product.

Thus, Japanese Patent Application JP-Kokai No. 73-86,612 describes the use of di(propylbenzyl)propylbenzene, the synthesis of which calls for a large number of reaction and separation stages due to the nonselectivity of a synthesis of this type.

Lastly, in Japanese Patent Application JP-Kokai No. 78-42,909 reference is made to the use, as a microencapsulation solvent, of the following isomers:

(i) ditolylphenylmethane,
(ii) tolyldiphenylmethane, and
(iii) tritolylphenylmethane.

The synthesis of each of these isomers calls for specific reactions, for example tolyldiphenylmethane from benzylidene chloride, toluene and benzene, followed by a separation of the isomers. Moreover, a mixture of these products must then be produced, and this is hardly advantageous from the standpoint of economy.

As a general rule, the prior art shows products for the microencapsulation solvent application of the monobenzylalkylbenzene or dibenzylalkylbenzene or, alternatively, di(alkylphenyl)phenylmethane type, but which can be manufactured only using relatively nonselective syntheses.

SUMMARY OF THE INVENTION

The present invention discloses products which are adapted for the microencapsulation solvent application and which have the advantage of being capable of being manufactured in a simple manner.

The present invention relates to polyarylalkane oligomer compositions consisting essentially of; preferably consisting of, a mixture of two oligomers A and B, wherein:

(a) the oligomer A is a mixture of isomers of formula:

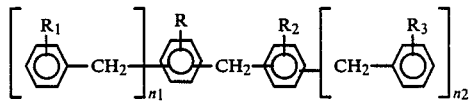

in which:

R is a linear or branched hydrocarbon chain containing n carbon atoms, and n is between 2 and 16, $R_1$, $R_2$ and $R_3$ are identical or different and selected from H or $CH_3$, and $n_1$ and $n_2$ each=0, 1 and 2, and $n_1+n_2 \leq 3$;

it being possible for each of the isomers A to have different substituents R, $R_1$, $R_2$ and $R_3$; and (b) the oligomer B is a mixture of isomers of formula:

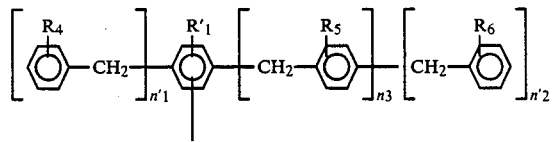

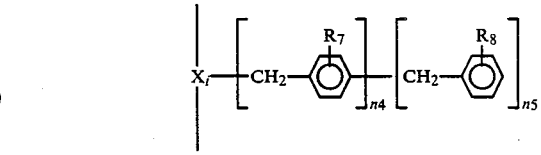

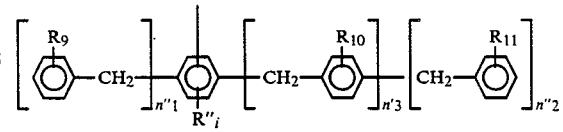

in which: $R'_i$ and $R''_i$ are identical or different and have the same meaning as R above, $R_4$, $R_5$, $R_6$, $R_7$, $R_8$, $R_9$, $R_{10}$ and $R_{11}$ are identical or different and selected from H or $CH_3$, $n'_1$, $n''_1$ and $n_4$ each=0, 1 or 2, $n'_2$, $n''_2$, $n_3$, $n'_3$ and $n_5$ each=0 or 1, $n'_1+n''_1+n'_2+n''_2+n_3+n'_3+n_4+n_5 \leq 2$, i has the value of 1 or 2, $X_i$ is a trivalent connecting group such as:

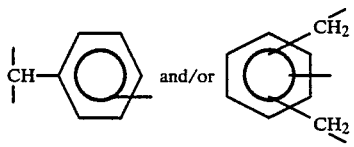

and in which the connections towards the groups

are provided by carbon atoms not forming part of the phenyl group of $X_i$;

each of the isomers B having the same or different substituents $R'_i$, $R''_i$, and $R_4$ to $R_{11}$.

That is to say, B may be a mixture of the products of formula (I) and (II) below, each of the products (I) and (II) itself being a mixture of isomers.

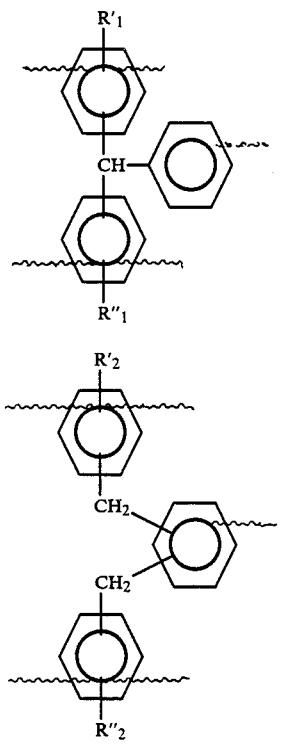

Among the compositions of the invention use is advantageously made of those where R, $R'_i$ and $R''_i$ are alkyls with n between 3 and 8, and preferably isopropyls.

Compositions in which $R_1$ to $R_{11}$ are hydrogen atoms are also advantageously employed.

Compositions in which $R_1$ to $R_{11}$ are hydrogen atoms and R, $R'_i$ and $R''_i$ are alkyls with n between 3 and 8, and preferably isopropyl groups, are also advantageously employed.

The particularly preferred compositions are such that:

(i) $R_1$ to $R_{11}$ are hydrogens,
(ii) R, $R'_i$ and $R''_i$ are isopropyls, and
(iii) i has the value of 1, that is to say that the connecting group $X_i$ is:

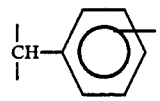

The compositions according to the invention exhibit all the properties which must be reconciled in microencapsulation solvents and it has been surprisingly found that these products are not odorants.

The invention also comprises the process of making the compositions as hereinafter set forth utilizing only chlorine, toluene and/or xylene and the product of formula:

in which Y is a linear or branched hydrocarbon chain containing from 2 to 16 carbon atoms, as starting materials. The product of formula (III) may also be a mixture of products which have different chains Y.

The invention also comprises microcapsules containing such compositions as hereinafter described.

DETAILED DESCRIPTION

A process for obtaining the oligomer compositions according to the invention is characterized in that, in a first stage, chlorine is reacted with toluene, xylene or a mixture of toluene and xylene by a radical reaction in the presence of a radical generator, and then any unreacted toluene or xylene is removed and, in a second stage, the reaction product from this first stage is subjected to the action of an inorganic halide or of an inorganic acid in the presence of a product of formula (III) or of a mixture of products (III) which have different chains Y. The starting hydrocarbon in the first stage is either toluene or xylene, or a mixture of toluene and xylene. The radical chlorination of the hydrocarbon is usually carried out at a temperature of between 50° and 110° C. and, better, between 70° and 100° C. It is preferably conducted so that only 10 to 30%, expressed as a molar percentage, of the hydrocarbon employed is converted into the corresponding chlorine derivative. The unconverted hydrocarbon is then removed, for example, by distillation. The free radical generator employed may be either a photochemical initiation or a chemical initiator. Among the chemical initiators there may be mentioned azo compounds such as azodiisobutyronitrile or else azodivaleronitrile, and peroxides such as, for example, lauroyl peroxide. The quantity of chemical initiator which is employed is generally between 0.05 and 3% by weight relative to the hydrocarbon employed, and preferably between 0.1 and 1.5%.

The reaction mixture obtained during the first stage is then subjected, in the presence of the product of formula (III), to the action of an inorganic halide, or else of an inorganic acid. In practice, this reaction takes place at a temperature of between 30° and 140° C., and preferably between 50° and 120° C.

A single product of formula (III) or a mixture of products (III) which have different chains Y may be employed.

The product (III) or mixtures thereof are advantageously added to the mixture obtained at the end of the first stage after the removal of the toluene and/or xylene.

Preferably, as many moles of product (III) are added as are removed in the form of toluene and/or xylene.

Among the inorganic halides, it is possible to employ ferric chloride, antimony trichloride, titanium tetrachloride or else aluminum chloride in weight concentrations, relative to the reaction mixture, which are generally between 50 ppm and 1%, and preferably between 100 ppm and 0.5%. Inorganic acids may also be employed, for example, sulphuric acid at a concentration of between 70 and 95% by weight. It is also possible to employ zeolites or, alternatively, certain inorganic oxides. An alternative form of the process in this second stage consists in pouring the reaction mixture from the first stage into the product (III) or the product (III) and the mixture of oligomers according to the invention, containing the inorganic halide or acid in the form of a solution or a dispersion. This alternative form is particularly advantageous for operating a continuous process of this kind, since it is obvious that this synthesis can be carried out noncontinuously or continuously.

After the excess product (III) has been distilled off, the removal of the inorganic halide or of the inorganic acid may be carried out by any known method such as washing with water, neutralizing and drying.

Toluene is advantageously employed in the first stage, and the groups $R_1$ to $R_{11}$ (in the oligomers according to the invention) are then hydrogen atoms, and $X_i$ is

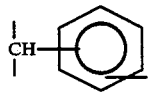

Advantageously, the product of formula (III) is an alkylbenzene with Y containing from 3 to 8 carbon atoms, and R, $R'_i$ and $R''_i$ are then alkyls. Isopropylbenzene (or cumene) is preferably employed; that is to say, that Y is an isopropyl group, and the groups R, $R'_i$ and $R''_i$ are then identical and denote an isopropyl group.

According to the process described, the mixture of polyarylalkane oligomers is generally obtained directly in the following proportions by weight:

A as a mixture of isomers:

$n_1+n_2=0$, between 56 and 90%, $n_1+n_2=1$, between 7 and 28%, $n_1+n_2=2$, between 1.5 and 8%, and $n_1+n_2=3$, between 0.1 and 3%.

B as a mixture of isomers:
$n'_1+n''_1+n'_2+n''_2+n_3+n'_3+n_4+n_5=0$,
between 1.1 and 5%, $n'_1+n''_1+n'_2+n''_2+n_3n'_3+n_4+n_5=1$,
between 0.25 and 1.5%, and $n'_1+n''_1+n'_2+n''_2+n_3+n'_3+n_4+n_5+2$, between 0.05 and 0.5%.

Depending on the use to which the mixture of polyarylalkane oligomers according to the invention is applied, it may be advantageous to perform a flash evaporation of this mixture to remove traces of impurities originating either from the starting materials or from the process, or having an incidental origin; in all cases the contents by weight do not exceed 1 to 2%. Among the pieces of equipment which can be employed, preference will be given to a thin-film evaporator; it must be reported, however, that, on an industrial scale, the technical performance of such equipment in respect of behavior under vacuum does not always allow all of the mixture of polyarylalkane oligomers to be recovered; these evaporated products nevertheless form an integral part of the invention, as is the case particularly with the isomers of the compound A for $n_1+n_2=3$ and of the compound B for $n'_1+n''_1+n'_2+n''_2+n_3+n'_3+n_4+n_5=2$.

The oligomer compositions of the present invention can be used to form microcapsules, such as for use in making carbonless transfer paper, by using the compositions to dissolve the dye; or other color-forming material requiring dissolving to be utilized, and forming the microcapsules in any conventional manner using conventional proportions of materials and reaction conditions. The oligomer compositions are used in those amounts necessary to properly dissolve the color-forming material. The outer rupturable encapsulating material can be any conventionally used for this purpose.

The invention will be further described in connection with the following examples which are set forth for purposes of illustration only.

EXAMPLE 1

368 g of toluene (4 moles) are placed in a reactor equipped with stirring means, a condenser, a chlorine feed tube and a Philips TLADK 30-watt lamp. 71 g of gaseous chlorine (1 mole) are then introduced while the temperature is maintained at 80° C. for 1 hour.

After stopping the photochemical initiation, the reaction mixture is placed in a 1-liter, three-necked round flask supporting an adiabatic glass column filled with a packing of glass helices (approximately 10 plates). The mixture is subjected to a fractional distillation under a vacuum of 50 mm of mercury so as to separate the unreacted toluene. The distillation is stopped when the toluene content at the foot of the column is below 0.2% (temperature equal to 100° C.).

The product recovered as the distillation residue is placed in a dropping funnel and is introduced over one hour into a reactor equipped with stirring means, containing 600 g of cumene (5 moles) and 60 mg of $FeCl_3$, at a temperature of 100° C. The whole is kept at 100° C., with stirring, for another one hour after the end of addition.

After cooling, the reaction mixture is washed with 10% hydrochloric acid and then with water until neutral and, lastly, the excess cumene is removed by distillation under a vacuum of 10 mm of mercury through a column of a few plates, so that the residual content of cumene in the bottom product is below 500 ppm (bottom temperature at the end of distillation=180° C.).

The mixture of polyarylalkane oligomers obtained has the following composition by weight:

| PRODUCT | $n_1 + n_2$ | | | | $n'_1 + n''_1 + n'_2 + n''_2 + n_3 + n_4 + n_5$ | | |
|---------|---|---|---|---|---|---|---|
|  | 0 | 1 | 2 | 3 | 0 | 1 | 2 |
| A | 68.8 | 20.8 | 4.2 | 2.5 | — | — | — |
| B | — | — | — | — | 2.4 | 1 | 0.3 |

And its formula is such that:

$R = R'_i = R''_i = CH(CH_3)_2$ $R_1$ to $R_{11} = H$ $i = 1$, that is to say $X_i$ is

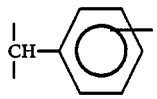

The overall weight yield calculated relative to the cumene which has reacted is 97%.

When subjected to a flash evaporation at 300° C. at 1 mm of Hg, this product gives, in a 95% yield, a mixture of polyarylalkane oligomers with a very faint odor and whose composition differs from that given above in the absence of the products corresponding to:

(i) A and $n_1 + n_2 \times 3$, and
(ii) B and $n'_1 + n''_1 + n'_2 + n''_2 + n_3 + n'_3 + n_4 + n_5 = 2$.

For a viscosity:

(i) at 20° C. = 9.5 cP, and (ii) at 40° C. +4.40 cP.

EXAMPLE 2

Operating under the same conditions of Example 1, but using 6 moles of toluene (592 g) for the photochlorination per 1 mole of chlorine and 9 moles of cumene in the coupling reaction, a mixture of polyarylalkane oligomers of the same formula as in Example 1 and having the following composition by weight is obtained:

| PRODUCT | $n_1 + n_2$ | | | | $n'_1 + n''_1 + n'_2 + n''_2 + n_3 + n_4 + n_5$ | | |
|---------|---|---|---|---|---|---|---|
|  | 0 | 1 | 2 | 3 | 0 | 1 | 2 |
| A | 83% | 11% | 2.8% | 0.7% | — | — | — |
| B | — | — | — | — | 2% | 0.4% | 0.1% |

The weight yield calculated relative to cumene is 98%.

When subjected to a flash evaporation at 300° C. at 1 mm of Hg, this product gives, in a 98% yield, a mixture of polyarylalkane oligomers with a very faint odor and whose composition differs from that given above in the absence of the products corresponding to:

(i) A and $n_1 + n_2 = 3$, and
(ii) B and $n'_1 + n''_1 n'_2 + n''_2 + n_3 + n'_3 + n_4 + n_5 = 2$.

For a viscosity:

(i) at 20° C. = 6.9 cP, and
(ii) at 40° C. +3.9 cP.

EXAMPLE 3

Operating under the same conditions as Example 1, but replacing the cumene with 5 moles of ethylbenzene (530 g) in the coupling reaction.

The polyarylalkane oligomer mixture obtained has the following composition by weight:

| PRODUCT | $n_1 + n_2$ | | | | $n'_1 + n''_1 + n'_2 + n''_2 + n_3 + n_4 + n_5$ | | |
|---------|---|---|---|---|---|---|---|
|  | 0 | 1 | 2 | 3 | 0 | 1 | 2 |
| A | 67 | 22.3 | 4.4 | 2.6 | — | — | — |
| B | — | — | — | — | 2.4 | 0.9 | 0.4 |

The weight yield calculated relative to ethylbenzene is 98%,

And a formula in which:

(i) R, $R'_i$, $R''_i = C_2H_5$,
(ii) $R_1$ to $R_{11} = H$,
(iii) $i = 1$, and
(iv) $X_i =$

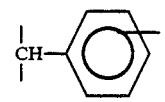

When subjected to a flash evaporation at 300° C. at 1 mm of Hg, this product gives, in a 96% yield, a mixture of polyarylalkane oligomers with a faint odor, whose composition differs from that given above in the absence of the products corresponding to:

(i) A and $n_1 + n_2 = 3$, and
(ii) B and $n'_1 + n''_1 + n'_2 + n''_2 + n_3 + n'_3 + n_4 + n_5 = 2$.

For a viscosity:

(i) at 20° C. = 6.9 cP, and (ii) at 40° C. +4.2 cP.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A polyarylalkane oligomer composition consisting essentially of the mixture of two oligomers, A and B, wherein:

(a) the oligomer A is a mixture of isomers of formula:

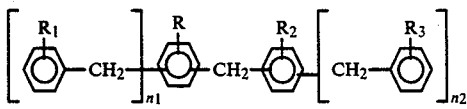

in which:

R is a linear or branched hydrocarbon chain containing n carbon atoms, and n is between 2 and 16, $R_1$, $R_2$ and $R_3$ are identical or different and from H or $CH_3$, and $n_1$ and $n_2$ each=0, 1 and 2, and $n_1+n_1+n_2 \leq 3$;

it being possible for each of the isomers A to have different substituents R, $R_1$, $R_2$ and $R_3$; and (b) the oligomer B is a mixture of isomers of formula:

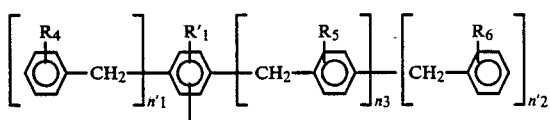

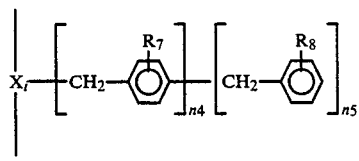

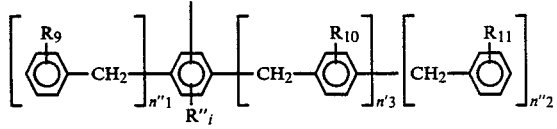

in which:

$R'_i$ and $R''_i$ are identical or different and have the same meaning as R above, $R_4$, $R_5$, $R_6$, $R_7$, $R_8$, $R_9$, $R_{10}$ and $R_{11}$ are identical or different and selected from H or $CH_3$, $n'_1$, $n''_1$ and $n_4=0$, 1, or 2, $n'_2$, $n''_2$, $n_3$, and $n'_3$ and $n_5$ each=0 or 1, $n'_1+n''_1+n'_2 n''_2+n_3+n'_3+n_4+n_5 \leq 2$, i has the value of 1 or 2, $X_i$ is a trivalent connecting group:

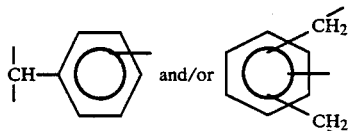

and in which the connections towards the groups

are provided by carbon atoms not forming part of the phenyl group of $X_i$, each of the isomers B having the same or different substituents $R'_i$, $R''_i$, and $R_4$ to $R_{11}$.

2. The composition of claim 1, wherein R, $R'_i$ and $R''_i$ are alkyl groups having 3 to 8 carbon atoms.

3. The composition of claim 1 or 2, wherein $R_1$ to $R_{11}$ are hydrogen atoms.

4. The composition of claim 1, wherein:

$R_1$ to $R_{11}$ are hydrogens,

R, $R'_i$ and $R''_i$ are isopropyl groups, and

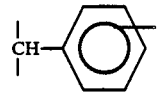

$X_i$ is:

5. The composition of claim 4, wherein the mixture of oligomers is in the proportions by weight of: A as a mixture of isomers: $n_1+n_2+=0$, between 56 and 90%, $n_1+n_2=1$, between 7 and 28%, $n_1+n_2=2$, between 1.5 and 8%, and $n_1+n_2=3$, between 0.1 and 3%; and B as a mixture of isomers:

$n'_1+n''_1+n'_2+n''_2+n_3+n'_3+n_4+n_5=0$, between 1.1 and 5%, $n'_1+n''_1+n'_2+n''_2+n_3+n'_3+n_4+n_5=1$, between 0.25 and 1.5%, and $n'_1+n''_1,+n'_2+n''_2+n_3+n'_3+n_4+n_5=2$ between 0.05 and 0.5%.

6. A process for the manufacture of the polyarylalkane oligomer compositions according to claim 1, comprising reacting, in a first stage, chlorine with toluene, xylene or a mixture of toluene and xylene in the presence of a radical generator, removing the unreacted toluene or xylene or the unreacted toluene and xylene, and, in a second stage, subjecting the reaction product from this first stage to the action of an inorganic halide or of an inorganic acid in the presence of a benzene-related compound of formula:

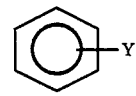

in which Y is a linear or branched hydrocarbon chain containing from 2 to 16 carbon atoms or a mixture of such benzene-related compounds.

7. The process of claim 6, wherein, in the first stage, only 10 to 30 mol % of the toluene or xylene or of the mixture of toluene and xylene which is employed is converted into a chlorine derivative.

8. The process of claim 7, wherein, in the first stage, chlorine is reacted with toluene.

9. The process of claim 8, wherein said benzene-related compound is an alkylbenzene with Y containing from 3 to 8 carbon atoms, or a mixture of such alkylbenzenes.

10. The process of any one of claims 6 to 9, wherein the benzene-related compound is cumene.

11. The process of any one of claims 6 to 9, wherein a flash evaporation is carried out on the product obtained in the second stage.

* * * * *